Figure 1:
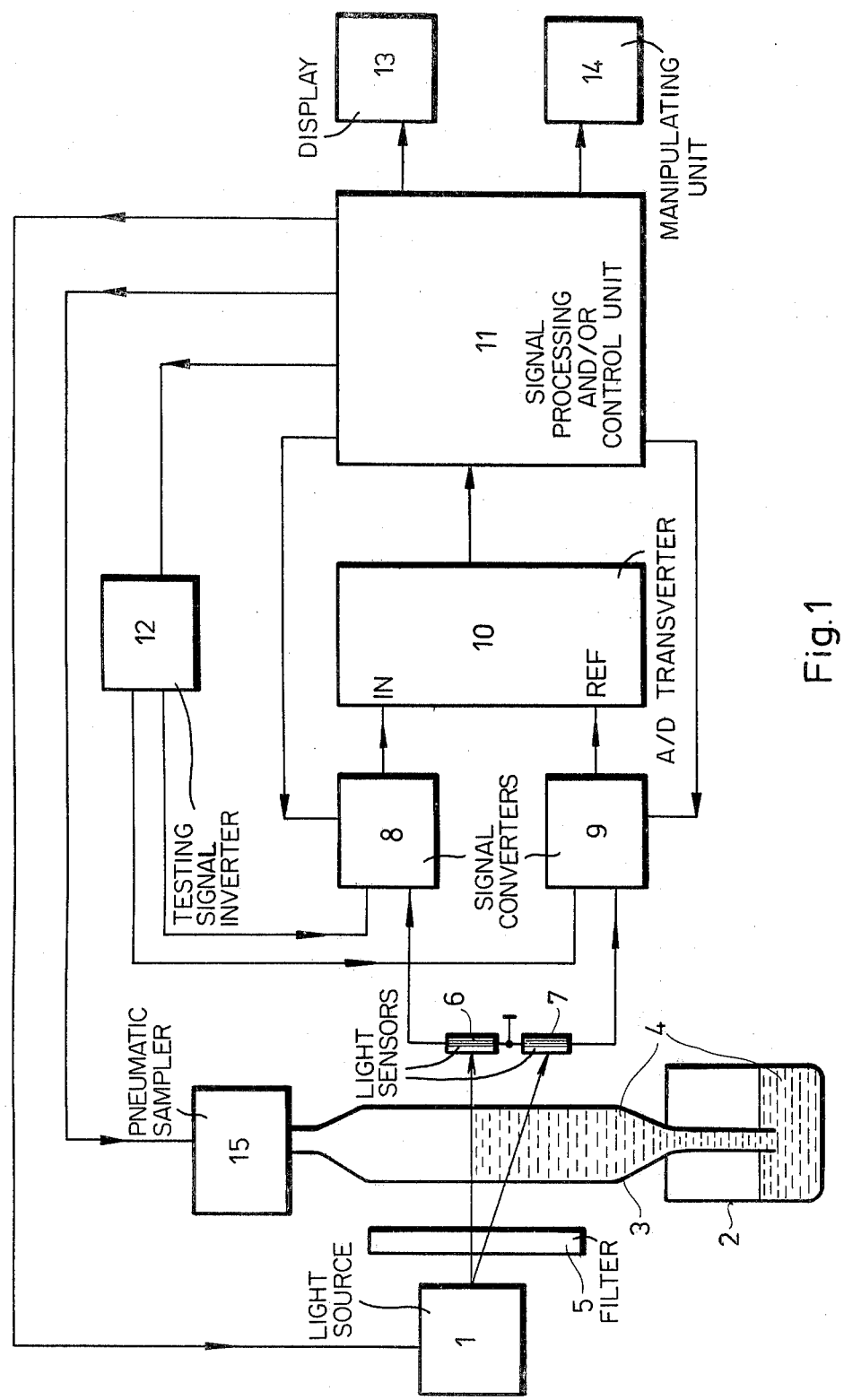

United States Patent [19]

Cserey et al.

[11] 4,417,812

[45] Nov. 29, 1983

[54] CIRCUIT ARRANGEMENT FOR DETERMINING THE CHARACTERISTICS OF LIQUIDS AND/OR GASES, IN PARTICULAR THE HEMOGLOBIN CONTENT OF THE BLOOD

[75] Inventors: László Cserey; Gábor Horváth; Tamás Szabados; Sándor Simonkay; János Sztipanovits; Pál Vimlati; Zoltán István; Pál Zillich, all of Budapest, Hungary

[73] Assignee: Medicor Muvek, Budapest, Hungary

[21] Appl. No.: 240,177

[22] Filed: Mar. 3, 1981

[51] Int. Cl.³ ..................... G01N 33/28; G01N 21/27
[52] U.S. Cl. ........................................ 356/40; 356/435
[58] Field of Search ................... 356/39–42, 356/320, 408–411, 434–435, 445, 448; 250/205

[56] References Cited

U.S. PATENT DOCUMENTS 3,531,209  9/1970  Williamson et al. ............... 356/409
4,180,327  12/1979  Maeda et al. ...................... 356/320

FOREIGN PATENT DOCUMENTS 55-125436  9/1980  Japan .................................. 356/410

Primary Examiner—William H. Punter
Attorney, Agent, or Firm—Young & Thompson

[57] ABSTRACT

A circuit arrangement for determining the characteristics of liquids and/or gases, in particular for determining the diverse parameters of blood. The equipment determines the ratio of the signals of the sensing element resp. of the signal converter at a double-light photometer and a reference, simultaneously performing constant or periodical testing, accordingly, the control of the whole measuring system can be ensured. Signal processing takes place by the expansion of series or cutoff point interpolating logarithm forming, by averaging; the system includes structural elements for performing adjustable error detection. The largest advantage of the circuit arrangement according to the invention lies in that the instabilities of the photometers of traditional construction may be eliminated, a higher measuring accuracy becomes possible, and by ensuring the testing possibilities, by performing a continuous self-control reliable measuring data are delivered.

3 Claims, 1 Drawing Figure

CIRCUIT ARRANGEMENT FOR DETERMINING THE CHARACTERISTICS OF LIQUIDS AND/OR GASES, IN PARTICULAR THE HEMOGLOBIN CONTENT OF THE BLOOD

It is a well known fact, that in course of measurements based on photometry extinction, absorption or transmission used to be determined on basis of the Beer-Lambert-law; the phenomena are namely proportional to the absorption of the light passing through the liquid sample to be tested, i.e. to the concentration of the component we are searching for.

In course of the known processes the value of extinction is read from the logarithmic scale and the value thus obtained is multiplied by a given factor, or in another case, in the course of signal processing a logarithmic amplifier is used for linearizing the characteristics which are proportional to the concentration. The absorption of the reagent(s) taking part in the colour reaction is determined in the same manner by using the so-called "blind-values", while the value of the same is substracted from the measuring results. All the methods and the instruments serving for performing these methods operate either with a direct analogous signal processing or A/D conversion with digital signal processing.

In order to be able to increase the stability of the measuring methods, the double method has been developed in such a manner, that besides the measuring channel a reference channel has been also used, in particular for compensating the instability of the light source. In order to increase accuracy of measurement, elimination of the disturbing factors is imperative, however, the solutions previously described do not always allow trouble-free measuring. Accordingly, the known equipment and methods are accompanied by several errors and do not enable the performance of high-accuracy measurements. For example we may refer to the drifts of the measuring reference channels, the necessity of ensuring short-time and long-time stability conditions and other errors, e.g. changes in linearity, unsteadiness of the zero point etc. The errors enumerated do not yield the possibility for the performance of high-accuracy measurements.

The object of this invention is to eliminate the accessory phenomena previously described that interfere with measuring and simultaneously increase the accuracy of the process.

The solution according to the invention, i.e. the circuit arrangement incorporates a double-light photometer; one of the rays of light coming from the light source strikes the sample to be tested, which has been previously sucked up into a measuring cuvette from the measuring receptacle. After having left the cuvette, the ray of light arrives at the light sensing element. The output of the light sensing element is connected to the input of the electric signal converter, while the output of the electric signal converter, while the output of the same is connected to one of the inputs of the A/D transverter. The other ray of light of the light source by-passes the sample, traverses the interference filter and strikes the reference light sensing element, the output of which is connected to the signal converter, while the output of the signal converter is connected to the other input of the A/D transverter. The digital surface of the A/D transverter is connected to the input of a signal processing and/or control unit, while the output of the same is connected to the input of the operating unit, to the light source, to the input of the testing D/A inverter, to the input of the display unit and to the input of the already mentioned measuring signal converter. The output of the testing D/A inverter is also connected to a further input of the measuring signal converter. It seems to be expedient to connect the pneumatic sampler to the signal processing and/or control unit, while the output of the sampler is connected to the measuring cuvette. The single figure of the drawing is a view showing the schematical arrangement of the equipment according to the invention.

In the drawing, one of the two rays of light radiated by the light source 1 arrives at the measuring cuvette 3, into which the sample 4 has been previously sucked from the measuring receptacle 2. Before traversing the sample to be tested in the measuring cuvette 3, the ray of light first of all traverses the interference filter 5 arranged before the measuring cuvette 3; after having left the measuring cuvette 3 it arrives at the light sensing element 6. The other ray of light radiated by the light source 1 by-passes the measuring cuvette 3 and after having traversed the interference filter 5 it arrives at the reference sensing element 7. The signals of the light sensing element 6 arrive at one input of the electric signal converter 8, from the output whereof they travel to one input (expediently to the input IN) of the A/D transverter 10, while the signals of the sensing element 7 arrive at one input of the signal converter 9 and from the output thereof they travel to the other input (expediently to the input REF) of the same A/D transverter 10. The converters 8 and 9 convert current to voltage.

In such a manner from the signals arriving at the A/D signal transverter 10 the proportional values of the actual values of the signal voltages $U_{XM}$ and $U_{ref}$ are formed; the value of the ratio appearing at the output of the A/D signal transverter equals $$D = U_{XM}/U_{ref}.$$

By forming directly said ratio the elimination of the disturbing factors—beginning from the light source via the light sensing elements, including the signal converters—may be eliminated, since in case of the simultaneous change of the signal voltages $U_{XM}$ and $U_{ref}$ the ratio thereof, i.e. the output value D remains constant.

The symmetry of the light sensing elements has been ensured as well for illumination as for thermocoupling, accordingly, supposing normal conditions, asymmetric change cannot occur in either of the channels, within the measuring range. For the supression of eventually occurring errors or failures, or for the control of the stable condition of the measuring system the signal converters 8,9 are operated in a switching mode of operation. The signal converters 8,9 are controlled by the signal processing and/or control unit 11, to which either a known signal level $U_{test}$ is connected from the testing inverter D/A 12 or an interpolation is performed previous to the measuring; hereafter the proportion of the levels of the values obtained from the signal converters 8,9 are controlled, which represents the ratio of the actual reference level and the measuring signal (i.e. the signal voltage $U_{ref}$ and the signal voltage $U_{XM+Utest}$). This ratio can be determined by the following correlation:

$$D \pm \Delta D = (U_{XM} \pm U_{test})/U_{ref} \qquad (1)$$

By applying the testing method, fundamentally four important controls may be performed, namely:

(1) Individual testing. By generalizing the individual test immediately before measuring, the faultless proper function of the whole detector system and the converters may be controlled.

(2) Test of linearity.

(3) Test of the complete electric processsing unit without the light sensing elements.

(4) Measuring the value of the reference-voltage.

Test of linearity and testing of the complete electric processing unit can be performed within the whole measuring range by generating discrete pulse trains by the aid of the signal processing and/or control unit 11, the testing D/A signal inverter and the signal converters 8, 9. The signal processing and/or control unit 11 has the function of storing in the course of the given test all the values belonging to the diverse samples and appearing on the output of the A/D transverter 10.

The accuracy of the test of linearity depends on the accuracy of the signal converters. The results of the test are controlled by means of the analogue-digital conversion and after the storage by digital comparison; the results must be within an interval of preselectably small tolerance and they, are displayed on the display 13. By self-testing the continuous control of the stable state of the measuring channel can be well performed.

Within the circuit arrangment according to the invention the logarithmic amplifier-increasing considerably the drift of the measuring channel and causing instability—has been omitted. Linearity of the value D is realized by the expansion in series with an optional number of the members, e.g. in compliance with the following correlation:

$$\ln D \approx \sum_{k=1}^{n} \frac{(1-D)^k}{k} \quad (2)$$

where n and k are either defined values or variables accompanying the choice of the measuring error, which can be either adjusted or determined by cutoff-point interpolating logarithmic routine, in this case the number of the cutoff points is either fixed or varying.

In such a manner, by increasing the value n or k the error of approximation of the function—the error of conversion—can be well reduced and manipulated.

The further advantage of the signal conversion lies in that the relative error remains approximately constant within the whole signal converting range.

In the case of logarithmic ampflifiers the error depends on the level and—similarly to the photometers provided with an indicator—it is the lowest at the highest measuring value, larger in the middle of the measuring range and it shows an increasing tendency towards the lower values.

Compared to the traditional methods, by means of the circuit arrangement proposed, two kinds of improvement may be realized: partly we are able to programme the measuring error, partly it may kept on a constant level within the whole measuring range, whereby towards the lower concentrations measuring errors may be considerably reduced. The series of expansion according to the correlation (2), i.e. the cutoff point interpolation and logarithmic routine may be realized by the aid of the circuit units CPU, ROM, RAM having been incorporated into the signal processing and/or control unit. By means of the equipment measuring accuracy may be further increased, in so far as the signal processing and/or control unit has an averaging routine, by the aid of which-in order to obtain the measuring accuracy needed-we form the mean value of m measurements, where the value of m is either fixed or varying, i.e. programmable. In respect to this case, the correlation described below is valid:

$$\bar{X}_M = \frac{\sum_{i=1}^{2^m} X_{Mi}}{2^m} \quad (3)$$

where $X_M$=the mean of the measurements, $X_{Mi}$=*the measure values/i . . . to m/*

Taking into consideration, that due to the quick conversions the complete measuring cycle is extremely short, by increasing the number of the measurements an optional statistical accuracy may be obtained.

When measuring unknown samples, the knowledge of the so-called blind-value $D_1$, i.e. the absorption of the light on the given wavelength of the applied reagent is of fundmental importance the value is stored in the equipment. This takes place in the following manner: the proper reagent is introduced into the measuring receptacle 2. The manipulating unit 14 actuates the pneumatic sampler 15 by means of the signal processing and/or control unit 11; the sampler sucks up the reagent into the measuring cuvette 3. The signal processing and/or control unit actuates the lamp of the light source 1, and after having performed self-control, the blind-value D is calculated as the average of several measurements and stored i.e. displayed on the display 13 in a programmable manner, by means of the manipulating unit 14 which is under the control of the control unit 11. The required modification of the blind-value $D_1$—or the zero value-can be performed at the manipulating unit 14 via the signal processing and/or control circuit 11, by modifying -the transfer function of the signal converter 8 or the transfer function is produced in the signal converter 8 by means of a potentiometer.

In order to be able to determine the concentration of any material contained in one volumetric unit, a constant or a calibrated value is needed, in which the concentration of the material tested is present in a known and accurate quantity. The substance with the standard concentration is put into the measuring receptacle 2, which may also contain the reagent. In a manner previously described, the level which is proportional to the absorption of the substance of known concentration on a given wavelength—i.e. the $D_3$ value-is measured. in such a manner the constant value characterizing the system and the concentration of a given substance may be defined as follows:

$$K \text{ (constant)} = \frac{\ln D_1 - \ln D_3}{X_H} \quad (4)$$

where $X_H$ stands for the nominal value of the concentration of the known calibrating substance.

The constant K is stored also by the signal processing and control unit 11 of the circuit arrangement, while the constant includes all the characteristics, which have to be taken into consideration in the course of photometry.

After having performed calibration, serial measurement of the unknown samples takes place; the values are idicated by the value $D_2$ and are formed in the signal processing and control unit 11 on the basis of the following correlation:

$$\overline{X}_M = \frac{\ln D_1 - \ln D_2}{K} \quad (5)$$

or by substituting the value of the constant $$\overline{X}_M = \frac{\ln D_1 - \ln D_2}{\ln D_1 - \ln D_3} \cdot X_H \quad (6)$$

By the proper modification of the value of the constant K the value $X_M$ can be directly displayed in the required concentration (g/e, mmol/l, etc); this factorizing may be programmed from the manipulating unit 14, but a built-in factorizing is also possible. When performing measurement on other substances, the values $D_1$ and $D_3$ i.e. the value of the constant is to be determined.

For measuring the light absorption of different materials on a given wavelength, the proper choice of the characteristics of the interference filter 5 and the light sensing elements 6, 7, of the spectral characteristics and the intensity of the light source 1, as well as of the value of the light absorption of the measuring cuvette 3 is absolutely necessary. Sensitivity and amplifying, respectively, can be realized by modifying the function of the signal converters 8, 9.

What we claim:

1. A circuit arrangement for determining the characteristics of fluids, comprising a double-light optical system (1), a measuring cuvette (3), an interference filter (5) disposed between the optical system and the cuvette and through which both lights from the optical system pass, two light sensing elements (6 and 7), two current-to-voltage converters (8 and 9), an A/D signal transverter (10), a signal processing and/or control unit (11), a testing D/A inverter (12), a display (13), a manipulating unit (14), and an automatic sampler (15), the cuvette dipping into a recptacle (2) for a fluid (4) to be tested, one of said lights passing through said cuvette (3) and striking one (6) of said light sensing elements, the other of said lights bypassing said cuvette (3) and striking the other (7) of said light sensing elements, said one (6) light sensing element being connected to an input of one (8) of said converters, said other (7) of said light sensing elements being connected to an input of the other (9) of said convertors, an output of each of said converters (8,9) being connected to a respective input of said signal transverter (10) which is in turn connected to an input of said signal processing and/or control unit (11), said signal processing or control unit (11) having separate outputs connected to said display (13) and to said manipulating unit (14) and to said optical system (1) and to said inverter (12) and to said sampler (15) and to each of said converters (8, 9), said inverter (12) also having separate outputs one connected to each of said converters (8, 9), said automatic sampler (15) having an output connected to said cuvette.

2. A circuit arrangement as claimed in claim 1, in which said signal processing and/or control unit (11) has the function of storing in the course of the given test all the values belonging to the diverse samples and appearing on the output of the A/D transverter (10).

3. A circuit arrangement as claimed in claim 1, in which said signal processing and/or control unit (11) preforms an averaging function.

* * * * *